(12) United States Patent
Nagel

(10) Patent No.: US 6,914,176 B1
(45) Date of Patent: Jul. 5, 2005

(54) CORN PRODUCTS AND METHODS FOR THEIR PRODUCTION

(75) Inventor: Bruce Nagel, Beaver Dam, WI (US)

(73) Assignee: Mycogen Plant Science, Inc, San Diego, CA (US)

(*) Notice: Subject to any disclaimer, the term of this patent is extended or adjusted under 35 U.S.C. 154(b) by 0 days.

(21) Appl. No.: 09/334,163

(22) Filed: Jun. 16, 1999

Related U.S. Application Data

(60) Provisional application No. 60/089,457, filed on Jun. 16, 1998.

(51) Int. Cl.[7] ............................ A01H 5/00; A01H 5/10; A01H 1/04; A01H 1/05
(52) U.S. Cl. ...................... 800/320.1; 800/264; 800/275
(58) Field of Search ................................ 800/264, 275, 800/320.1, 298, 260, 278, 281

(56) References Cited

U.S. PATENT DOCUMENTS

| | | | |
|---|---|---|---|
| 5,380,831 A | | 1/1995 | Adang et al. |
| 5,569,820 A | * | 10/1996 | Stelpflug et al. .......... 800/320.1 |

FOREIGN PATENT DOCUMENTS

| | | |
|---|---|---|
| WO | WO9201367 | 2/1992 |

OTHER PUBLICATIONS

Lee, The Maize Handbook, M. Freeling, V. Walbot, eds., 1994, Springer–Verlag, New York, pp. 423–424.*
Pamin et al. Genetic variation and selection response for oil composition in corn. Crop Science, vol. 26, pp. 279–282, 1986.*
Dunlap, F.G., White, P.J., Pollak, L.M., Brumm, T.J. (1995) "Fatty acid composition of oil from adapted, elite corn breeding materials," *Journal of the American Oil Chemists Society*, vol. 72(9):981–987.
Jellum, Milton D. (1970) "Plant Introduction of Maize as a Source of Oil with Unusual Fatty acid Composition" *J. Agr. Food Chem.*, vol. 18, No. 3:365–370.
Jellum, M.D. and R.E. Worthington (1966) "A Rapid Method of Fatty Acid Analysis of Oil from Individual Corn (*Zea mays* L.) Kernels" *Crop Sci.* 6:251–253.
Coe et al. (1988) "Corn and Corn Improvement" (3d ed.), Sprague and Dudley, Eds., pp. 142–143; 195–198; and 206–209 (American Society of Agronomy, Madison, WI).
Vineyard, M.L. and Robert P. Bear (1952) *Maize Genetics Cooperation Newsletter* 26:5.
Nelson et al. (1965) "Second Mutant Gene Affecting the Amino Acid Pattern of Maize Endosperm Proteins" *Science* 150:1469–1470.
Mains, E.B. (1926) "Studies in Rust Resistance" *The Journal of Heredity* 17:313–325.
Mains, E.B. (1931) "Inheritance of Resistance to Rust, *Puccinia sorghi*, in Maize" *J. Agric. Res.* 43:419–430.

Wilkinson, D.R. and A.L. Hooker (1968) "Genetics of Reaction to *Puccinia sorghi* in Ten Corn Inbred Lines from Africa and Europe" *Phytopathol.* 58:605–608.
Saxena, K.M.S. and A.L. Hooker (1968) "On the Structure of a Gene for Disease Resistance in Maize" *Proc. Nat'l Acad. Sci. USA* 61:1300–1305.
Ullstrup, A.J. (1965) "Inheritance and Linkage of a Gene Determining Resistance in Maize to an American Race of *Puccinia polysora*" *Phytopathol.* 55:425–428.
Nelson, Oliver E. and A.J. Ullstrup (1964) "Resistance to Leaf Spot in Maize" *J. Heredity* 55:195–199.
Hamid, A.H. and R.R. Hill, Jr. (1982) "Host x Isolate Interactions in Corn Inbreds Inoculated with *Cochliobolus carbonum* Race 3" *Phytopathol.* 72:1169–1173.
Smith, D.R. and A.L. Hooker (1973) "Monogenic Chlorotic–Lesion Resistance in Corn to *Helminthosporium maydis*" *Crop Sci.* 13:330–331.
Hooker, A.L. (1963) "Monogenic Resistance in *Zea mays* L. to *Helminthosporium turcicum*" *Crop Sci.* 3:381–383.
Hooker, A.L. (1977) "A Second Major gene Locus in Corn for Chlorotic–Lesion Resistance to *Helminthosporium turcicum*" *Crop Sci.* 17:132–135.
Hooker, A.L. (1981) "Resistance to *Helminthosporium turcicum* from *Tripsacum floridanum* incorporated into corn" *Maize Genetics Coop. Newsletter* 55:87–88.
Couture et al. (1971) "Role of cyclic hydroxamic acids in monogenic resistance of maize to *Helminthosporium turcicum*" *Phys. Plant Pathol.* 1:515–521.
Chang, Siew–Hoong and James L. Brewbaker (1976) "The genetics of resistance to the corn leaf aphid, *Rhopalosiphum maidis* (Fitch)" *Maize Genetics Coop. Newsletter* 50:31–32.
Brewbaker, James L. (1974) "Continuous Genetic Conversions and Breeding of Corn in a Neutral Environment" *Proc. 29th Ann. Corn & Sorghum Res. Conf.* pp. 118–133.
Pfund, J.H. and C.W. Crum (1977) "Inheritance of Tolerance to Eradicane in Maize" *Agronomy Abstracts* p. 66.
Miranda, Liuz Torres de (1981) "Allometric genetics" *Maize Genet. Coop. Newsletter* 55:18–19.
Miranda et al. (1982) "Genetics of environmental resistance and super–genes" *Maize Gene. Coop. Newsletter* 56:28–30.
Schwartz, Drew (1950) "The Analysis of a Case of Cross–sterility in Maize" *Proc. Nat. Acad. Sci. USA* 36:719–724.
Schwartz, Drew (1951) "Gamete factor" *Maize Gene. Coop. Newsletter* 25:30.
Poehlman, John Milton (1979) *Breeding Field Crops* (2d ed.), AVI Publishing Co. pp. 292–295.

* cited by examiner

*Primary Examiner*—David T. Fox
*Assistant Examiner*—Cynthia Collins
(74) *Attorney, Agent, or Firm*—Eric Kraus

(57) ABSTRACT

Disclosed herein is a subgroup of corn lines comprised of plants that produce seeds having low saturated fatty acid content. The plants disclosed herein can be used to produce low saturated corn material predictably, via conventional methods. Further, the plants disclosed herein can be used to produce commercially acceptable hybrids having lower saturated fat content.

19 Claims, No Drawings

US 6,914,176 B1

CORN PRODUCTS AND METHODS FOR THEIR PRODUCTION

This application is a continuation of provisional application Ser. No. 60/089,457 filed Jun. 16, 1998.

BACKGROUND OF THE INVENTION

In recent decades, it has become increasingly clear that diets containing large amounts of saturated fatty acids are directly correlated to an increased likelihood of developing heart disease. Hence, efforts have been made to modify the fatty acid content of commonly used oils to produce healthier oils having lower amounts of saturated fatty acids.

Corn oil is composed of saturated and unsaturated fatty acids with carbon chain lengths ranging from 12 to 24. Approximately 95% or more of the total oil content is composed of palmitic (16:0), stearic (18:0), oleic (18:1), and linoleic (18:2) acids, Jellum (1970) *J. Agric. Food Chem.*, 18:365–70. Palmitic and stearic acids are saturated fatty acids; thus, corn oil having less of these two fatty acids would be highly desirable.

The published literature on saturated fatty acid content in corn indicates the presence of diverse genes, located on different chromosomes, that affect saturated fatty acid content in a manner not clearly understood. This fact, combined with the virtual absence of information regarding the molecular biology of fatty acid profile in corn, has complicated the task of modifying the saturate level in corn and, in particular, has rendered the breeding endeavor of selecting for corn saturate content highly unpredictable a priori. Moreover, there has been no basis to date for a reasonable expectation of success in obtaining mean saturate levels less than 8%.

BRIEF SUMMARY OF THE INVENTION

In general, the present invention relates to corn material having a saturated fatty acid (saturate) content less than the lowest values previously reported, and to a corn oil having a percentage of saturates that provides for a more desirable and healthier oil.

More specifically, the present invention relates to corn seeds which have a saturate content of less than about 7.0% by weight relative to the total fatty acid content of the seed (hereinafter expressed as percent by weight, or simply percent). In the most preferred embodiment, the seed has a saturate content of less than about 6.0%. The invention further relates to a corn plant which produces seeds having a mean saturate content of less than about 7.0% by weight. Yet another aspect of the present invention is directed to a corn oil having a saturate content less than about 7.0%.

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. Unless indicated otherwise, respective contents of the documents cited are hereby incorporated by reference.

Percentages and ratios given herein are by weight, and temperatures are in degrees Celsius unless otherwise indicated. The references cited within this application are herein incorporated by reference to the extent applicable. Where necessary to better exemplify the invention, percentages and ratios may be cross-combined.

DETAILED DISCLOSURE OF THE INVENTION

In order to provide an understanding of a number of terms used in the specification and claims herein, the following definitions are provided.

"Selection"—Occurs when plants with desired phenotypes or genotypes are chosen for additional plant breeding procedures and breeding projects.

"Intermating"—Denotes the practice of planting seeds of selected plant phenotypes in individual rows, such that normal germination, emergence and plant maturation occur, and (at the onset of pollen-shed and silk extrusion) systematically crossing plants from each of these rows to plants from as many other rows as possible, thereby to maximize the number of crosses between unrelated individuals in the population.

"Backcrossing"—as used herein refers to the crossing of a progeny plant or line with its parent plant or line.

"Variety"—Refers to a group of plants within a species, such as *Zea mays* L., which share certain constant characters that separate them from other possible varieties within that species. While possessing at least one distinctive trait, a variety can also be characterized by a substantial amount of variation between individuals within the variety, based primarily on the Mendelian segregation of traits among the progeny of succeeding generations.

"Line"—a line as distinguished from "variety" and "cultivar" refers to a group of plants which are substantially uniform in their traits except that there is relatively minor variation within the group and such variation can be characterized. The decreased variation within this group has generally (although not exclusively) resulted from several generations of self-pollination (selfing).

"True Breeding"—A line is considered "true breeding" for a particular trait if it is genetically homozygous for that trait to the extent that when the variety is self-pollinated, no significant amount of independent segregation of the trait among progeny is observed.

"Saturate Content" and "Saturates"—These terms are used synonymously and interchangeably with relation to measurements of the proportion of saturates to total fatty acids present in corn oil which is extracted from single seeds (using the whole- or half-seed technique, as described below) or from bulked seed. Since the saturate values set out in this description are generally obtained from GLC analyses, the reported proportions of saturate are essentially by weight. When saturate content or saturate value are expressed as a percent or a percent by weight, it is to be understood that such percentage is relative to the total fatty acid content of the seed(s).

"Bulked Seed"—can be constituted, for example, from a plurality of seeds of a single cob (a kernel bulk"), from the combined seed from all or a particular part of a genetically related family of plants, or from the seed of a plant introduction (defined below).

A "Plant Introduction" (P.I.)—is a sample of seeds of a given species (e.g., *Zea mays* L.) that can be grown into plants having a common discernible (gross) morphology. Generally designated by country of origin, a P.I. often represents germplasm native and/or adapted to that country, and hence may embody considerable genetic variability. A P.I. can also represent the germplasm of an inbred line.

The following examples are provided to further illustrate the present invention and are not intended to limit the invention beyond the limitations set forth in the appended claims.

EXAMPLE 1

Determination of Fatty Acid Content

The screening can be effected, for example, by a half-seed technique, in which the seed scutulum is excised and the oil extracted is assayed by GLC, see Jellum & Worthington (1966) *Crop Sci.* 6:251–253, or by similarly analyzing oil extracted from a whole seed. The latter approach does not save the embryo for germination. GLC analysis can be conducted on a five- (or more) kernel bulk sample and on a one-half kernel sample, which allows the planting of the remaining half-seed for further breeding. The screening can be performed before an initial selfing step or, if a greater degree of segregation is desired, after a self-pollination of plants grown from the bulk seed.

The fatty acid composition of corn seeds developed in the breeding program was determined by GLC in accordance with the procedures described below.

The oil was obtained by using a corn oil extraction protocol having the following steps:

1. A sample of corn kernels were removed from the ear and was then catalogued according to row number and pedigree.

2. A sample was crushed with a pestle in a mortar. Ether was added and the sample was crushed further for ten seconds.

3. This solution was then drawn up through non-absorbing cotton into a pipette. The clean solution was then put into a test tube.

4. Three drops of tetramethylammonium hydroxide or sodium methoxide were added to the solution in the test tube and allowed to react for five minutes.

5. After five minutes, distilled water was added to the solution to raise the liquid level in the test tube. Since oil is lighter than water, the oil was easily siphoned off the top layer.

6. The oil drawn off was placed in 2 ml vials. Ether was added to raise the level to three-fourths full.

7. The vial was then capped and thus ready to be processed through the gas liquid chromatograph.

For analyses of one-half seed samples, a small piece of the scutellum was removed with a razor blade. A sample of scutellar tissue was then placed in a mortar with a small amount of ether, approximately 1 to 1.5 ml. The sample was crushed and stirred for approximately 10 seconds with a pestle, and the solution drawn up through non-absorbent cotton and placed in a test tube. A 0.5 ml sample of the ether extractant was then treated in the manner described above. The fatty acid analysis of one half-seed allowed planting of the remaining half-kernel in a breeding nursery and conducting of additional research and development with this genotype.

The GLC analyses were accomplished using a 5890A Hewlett-Packard gas liquid chromatograph equipped with a flame ionization detector and a Hewlett-Packard 3396A integrator. The column used was a Supelco 2330 fused silica capillary column (having a film thickness of 0.2 micron and column dimensions of 15 m.x0.25 mm.). The operating conditions for the GLC analysis included an injector temperature of 250 degrees Celsius and a detector temperature of 300 degrees Celsius. Column flow was 2.0 ml/min. of helium. Each chromatographic run was temperature-programmed to begin at 170 degrees Celsius and remain at that temperature for 1.0 min. The temperature was then increased to 180 degrees Celsius at a rate of 1 or 2 degrees Celsius/min. After this period of time, the chromatograph was completed and the column prepared for the next run.

EXAMPLE 2

Production of Mutant Lines

Two high oleic corn lines from the source population HOLEISYN were selected to see if low saturate lines could be developed. These two lines were crossed and the F1 seed was grown and selfed. The F2 seed was planted, and before pollination, approximately 200 ears were shootbagged. Tassels that were shedding were selected and the ear shoots were cut back to ensure good silk exposure. A day later the corn pollen was collected using tassel bags. The pollen was placed on a small screen to filter out pollen from anthers and other foreign material. The pollen was then poured into a solution of 1 ml EMS and 100 mls Fisher parafin oil (stock diluted by 1 ml and 15 mls oil solution). The solution was mixed every minute for the first five minutes and then every five minutes for 45 minutes to keep the pollen suspended. After 45 minutes the pollen/parafin solution was brushed onto the silks of developing ears. A tassel bag was used to cover the ear to prevent contamination. The ear was picked at maturity and then tested for fatty acid content using the half-seed GLC analysis procedures outlined above.

EXAMPLE 3

Mutant Seed Production in Greenhouse

Resulting seeds from the EMS mutagenesis procedure were screened for low saturate content. Plants derived from half seeds designated as lines LS1498-18, LS288-04, and L0417-12 which showed promising levels of saturates and oleic acid were selfed to produce sufficient seed for these experiments. As soon as fully mature seed could be harvested from plants derived from this seed, five kernels from each plant were subjected to fatty acid methyl ester (FAME) analysis to determine fatty acid profiles. Saturates levels were then determined and statistical analysis was performed to identify those sublines (tracing back to individual selfed plants) which were significantly lower in total saturates. Seeds from these identified sublines were planted and selfed to produce another cycle of seed which was then analyzed. Numerous sublines were generated for each mutant line; however, only a few examples have been presented in Table 1. Results of sublines showed total saturates were always below the levels found in elite germplasm, i.e., OQ414. The lowering of saturates in the mutant germplasm was accomplished by up to a 50% reduction in 16:0 levels (palmitic acid), rather than 18:0 levels (stearic acid) when compared back to levels found in conventional germplasm. Presence of high 18:1 levels in the mutants was observed and consistent with earlier efforts to breed for high oleic acid in maize. The 18:2 levels (linoleic acid) were shown to be considerably lower in the mutants compared to elite germplasm while 18:3 (linolenic acid) and percent lipids of the seed embryo remained fairly constant.

EXAMPLE 4

Mutant Seed Production in Field

Greenhouse produced seed from the lines produced in Example 2 was pooled across several sublines within each mutant line in order to supply a sufficient number of kernels for planting. Plants were selfed and fatty acid content was analyzed. About a 15% further reduction in saturates was observed from field produced seed compared to kernels from the greenhouse. Greenhouse produced seed had total saturate levels between 7.7% and 8.8%, whereas the field produced seed had saturate levels below 7% (Table 2). These results seemed to be consistent with observations of Canola seed which showed 1–2% reduction in saturates for field compared to greenhouse grown seed.

TABLE 1

Percent fatty acid profiles for three mutant lines and sublines derived therefrom

| Mutant Line | Total Saturates (%) | 16:0 (%) | 18:0 (%) | 18:1 (%) | 18:2 (%) | 18:3 (%) | Lipids of seed embryo (%) |
|---|---|---|---|---|---|---|---|
| LS1498-18[1] | 5.6 | 4.4 | 1.2 | | | | |
| LS1498-18.S01 | 7.3[2] | 5.8 | 1.4 | 64.3 | 26.1 | 0.7 | 25.4 |
| | 0.2[3] | 0.1 | 0.2 | 2.4 | 2.4 | 0.1 | 10.3 |
| LS1498-18.S01.S08 | 6.7[2] | 5.5 | 1.2 | 64.9 | 26.4 | 0.8 | 26.7 |
| | 0.1[3] | 0.2 | 0.1 | 0.8 | 0.7 | 0.1 | 0.6 |
| LS288-04[1] | 7.4 | 5.4 | 2.0 | | | | |
| LS288-04.S09 | 7.5[2] | 5.2 | 2.3 | 65.1 | 25.8 | 0.5 | 27.9 |
| | 0.2[3] | 0.1 | 0.2 | 1.2 | 1.2 | 0.0 | 5.9 |
| LS288-04.S09.S06.S02 | 6.9[2] | 4.9 | 2.0 | 71.1 | 19.9 | 0.7 | 34.8 |
| | 0.2[3] | 0.2 | 0.1 | 1.3 | 1.3 | 0.1 | 4.5 |
| LS0417-12[1] | 6.8 | 5.0 | 1.8 | | | | |
| LS0417-12.S07 | 9.0[2] | 6.8 | 2.2 | 68.2 | 20.5 | 0.8 | 26.7 |
| | 0.3[3] | 0.3 | 0.1 | 1.3 | 1.1 | 0.1 | 5.4 |
| LS0417-12.S07.S08 | 7.6[2] | 5.8 | 1.8 | 72.4 | 18.1 | 0.7 | 27.7 |
| | 0.1[3] | 0.1 | 0.1 | 1.7 | 1.7 | 0.0 | 1.8 |
| OQ414 | 12.0[2] | 10.8 | 1.2 | 23.4 | 62.7 | 1.1 | 28.2 |
| | 0.5[3] | 0.6 | 0.1 | 1.4 | 0.9 | 0.1 | 4.2 |

[1]Original mutant line
[2]Average of five kernels
[3]Standard deviation

TABLE 2

Fatty acid composition of greenhouse and field produced mutant seed

| Mutant Line | Total Saturates (%) | 16:0 (%) | 18:0 (%) | 18:1 (%) | 18:2 (%) | 18:3 (%) | Lipids of seed embryo (%) |
|---|---|---|---|---|---|---|---|
| LS1498-18 (Greenhouse)[1] | 7.7[2] | 5.8 | 1.9 | 70.8 | 20.1 | 0.6 | |
| | 0.4[3] | 0.2 | 0.2 | 1.8 | 2.1 | 0.0 | |
| LS1498-18 (Field) | 6.3[4] | 4.9 | 1.4 | 64.9 | 27.4 | 0.6 | 33.1 |
| | 0.3[5] | 0.1 | 0.3 | 0.8 | 0.8 | 0.0 | 2.5 |
| LS288-04 (Greenhouse) | 8.0[2] | 5.3 | 2.7 | 67.0 | 23.6 | 0.5 | |
| | 0.1[3] | 0.1 | 0.1 | 0.5 | 0.4 | 0.0 | |
| LS288-04 (Field) | 6.4[4] | 4.3 | 2.1 | 69.6 | 22.7 | 0.5 | 35.8 |
| | 0.3[5] | 0.2 | 0.4 | 1.2 | 1.3 | 0.1 | 6.3 |
| LS0417-12 (Greenhouse) | 8.8[2] | 6.8 | 2.0 | 67.5 | 22.0 | 0.6 | |
| | 0.1[3] | 0.2 | 0.2 | 2.3 | 2.2 | 0.1 | |
| LS0417-12 (Field) | 6.7[4] | 5.5 | 1.2 | 66.0 | 25.8 | 0.7 | 36.6 |
| | 0.4[5] | 0.4 | 0.1 | 3.1 | 2.8 | 0.1 | 7.2 |

[1]Seed pooled from several sublines
[2]Average of means
[3]Standard error
[4]Average of five kernels
[5]Standard deviation Seeds of the lines disclosed herein are deposited with the American Type Culture Collection, 12301 Parklawn Drive, Rockville, Md.) 20852 USA, in accord with the provisions of the Budapest Treaty. Cultures were assigned the following accession numbers by the repository: LS1498, ATCC No. PTA-1396 (deposited Feb. 22, 2000); LS288, ATCC No. PTA-3642 (deposited Aug. 16, 2001); LS0417, ATCC No. PTA-1397 (deposited Feb. 22, 2000).

EXAMPLE 5

Production of Commercially-acceptable Hybrids and Hybrids Having Waxy Type Kernel Elite low saturate corn lines can be developed by crossing the low saturate line (derived from a low saturate P.I. population) with an agronomically elite line for a given maturity region. For example, CS40S is an elite corn inbred line which has a saturate content of about 11.4%. LS288-04-506-502 is the designation for a low saturate line developed by the procedures of this invention. By crossing CS405 with LS288-04-506-502, followed with two to four generations of selfing and selection of low saturate lines with agronomically desirable traits, the lines resulting from this breeding effort can exhibit low saturate content along with acceptable agronomic traits such as plant vigor, good stalks and roots, disease resistance, and the like. Crossing low saturate lines with a number of elite lines and selfing and selecting from these crosses can produce numerous new low saturate corn lines. These lines can be adapted to any maturity region desired by selecting the appropriate maturity level in the elite corn parent and selecting for the desired maturity in subsequent selfing generations. The low saturate lines developed by the present invention can be used as one or more parents in corn hybrids.

Also, one or more backcrosses to the elite recurrent parent can be accomplished to incorporate a higher percentage of the elite germplasm characteristics while retaining the low saturate trait.

An inbred line that is true-breeding for a low saturate phenotype according to the present invention is advantageously employed in a backcrossing program to introgress the low saturate trait into other, more agronomically desirable lines. For example, a true-breeding inbred line of the present invention can be the donor parent for backcrossing to a waxy corn line, to thereby produce a high oleic, low saturate, waxy hybrid or line. In this regard, a "hybrid" would be an offspring obtained by crossing parent plants of different lineage.

As disclosed, for example, by Coe et al., in Corn and Corn Improvement (3d ed.), Sprague, G. F. and Dudley, J.

W., Eds., p. 142–143 (American Society of Agronomy, Madison, Wis., 1988) (hereinafter "Coe et al. (1988)"), the waxy type of kernel is so unique and its expression so unconfounded that the waxy trait is conventionally used as a universal marker. The waxy endosperm chips away evenly when cut with a blade, leaving a smooth, opaque surface, while normal endosperm breaks unevenly and leaves an irregular, translucent surface. In addition, the starch in the outer surface of a non-waxy endosperm stains blue, turning quickly to black, with an iodine ($I_2$)-potassium iodide (KI) solution, while that of material homozygous for the waxy allele (wx1) stains reddish brown, turning soon to dark brown.

The uniqueness of the waxy trait allows for the ready backcrossing to a recurrent waxy parent of progeny that are (low saturate x waxy) hybrids, according to the present invention, against a donor waxy (wx1/wx1) parent. That is, progress can be readily monitored for a backcrossing generation whereby the germplasm contribution of the low saturate donor, save for the expression of a mean saturate value of about 7% or less, is virtually eliminated.

Introgression of a low saturate phenotype as described above can also be accomplished with regard to genetic backgrounds characterized by traits other than waxy. Illustrative of traits that could be combined with a low saturate phenotype, pursuant to the present invention, are those listed in Table 3.

TABLE 3

EXEMPLARY CORN TRAITS TO COMBINE
WITH LOW SATURATE PHENOTYPE

| Determinant* | Description |
|---|---|
| Insect Resistance | |
| Bt | the expression of Bt genes, synthetic or native, can impart insect resistance to a wide array of insects. See e.g., U.S. Pat. No. 5,380,831 whose teachings are incorporated herein in their entirety. |
| Endosperm Mutants | |
| ael[S] | "amylose extender": amylose fraction of starch increased to 50% (glassy, tarnished endosperm); ael gene plus modifiers provides a range in amylose from about 50% to 80%, but the amylose content can be stabilized at intermediate levels; Vineyard & Bear (1952) Corn Genet. Coop. Newsltr. 26:5 |
| o2[S] | "opaque-2 endosperm": reduced zein and increased lysine in endosperm (soft, chalky, non-transparent kernels; little, hard, vitreous or horny endosperm); Nelson et al. (1965) Science 150:1469–70 |
| Resistance to Common Leaf Rust (*Puccinia sorghi*): | |
| Rp1 | Mains (1926) J. Hered, 17:313–25; (1930) J. Agric. Res. 43:419–30 |
| Rp3[S] | Wilkinson & Hooker (1968) Phytopathol. 58:605–08 |
| Rp4[S] | Wilkinson & Hooker (1968) loc. cit. |
| Rp5[S] | Saxena & Hooker (1968) Proc. Nat'l Acad. Sci. USA 61:1300–05 |
| Rpp9[S] | resistance to southern leaf rust (*Puccinia polysora* Underw.); Ullstrup (1965) Phytopathol. 55:425–28 |
| Resistance to Northern Leaf Spot (*Cochliobolus carbonum* Nelson): | |
| Hm1 | confers full resistance, although some alleles are intermediate; Nelson & Ullstrup (1964) J. Hered. 55:194– |
| Hm2 | confers resistance, in the presence of homozygous recessive hm1, that is lower initially but becomes progressively stronger as the plant develops. Nelson & Ullstrup (1964) J. Heredity 55:194–99, Hamid et al. (1982) Phytopathol. 752:1169–73 |

TABLE 3-continued

EXEMPLARY CORN TRAITS TO COMBINE
WITH LOW SATURATE PHENOTYPE

| Determinant* | Description |
|---|---|
| Resistance to Southern Corn Leaf Blight (*Bipolaris maydis*) (Nisik.) Shoemaker (race 0): | |
| rhm1[S] | Smith & Hooker (1973) Crop Sci. 13:330–31 |
| Resistance to Northern Leaf Blight (*Helminthosporium turcicum* Pass.): | |
| Ht1[S] | Hooker (1963) Crop Sci. 3:381–83 |
| Ht2[S] | Hooker (1977) loc. cit. 17:132–35 |
| Ht3[S] | Hooker (1981) Corn Genet. Coop. Newsltr. 55:87–88 |
| Bx1 | resistance to *H. turcicum* (reduces levels of *H. turcicum* infection in genotypes ht1/ht1 Bx1/Bx1 and Ht1/Ht1/Bx1/Bx1, relative to bx1/bx1 counterparts); Couture et al. (1971) Phys. Plant Pathol. 1:515–21 |
| Aphid, Corn, Mosaic, Virus I, Eradicane ™ Herbicide, Drought, Heat & Aluminum Tolerance | |
| aph1 | resistance to corn leaf aphid (*Rhopalosiphum maidis* Fitch.); Change & Brewbaker (1976) Corn Genet. Coop. Newsltr. 50:31–32 |
| Mv1 | resistance to corn mosaic virus I; Brewbaker (1974) in Proc. 29th Ann. Corn & Sorghum Res. Conf. 118–33 |
| thc1 | tolerance to Eradicane ™ (S-ethyl-dipropylthiocarbamate plus R25788 safener); Pfund & Crum (1977) Agronomy Abstr., p. 66 |
| lte1 | Miranda (1981) Corn Genet. Coop. Newsltr. 55:18–19 (also conditions frost resistance) |
| Lte2 | Miranda (1982) loc. cit. 56:28–30 |
| Conditions pollen competition, disfavoring fertilization of silks with same genotype by pollen of another (Gal-S pollen outcompetes gal pollen for Gal-S silks); maintains isolation of strains from outcrossing | |
| Gal-S[S] | D. Schwartz (1950) Proc. Nat. Acad. Sci. USA 36: 719–724 |
| GA8 | Schwartz (1951) Corn Genet. Coop. Newsltr. 25:30 |

*Designation of determinations conforms to usage in linkage map of Coe et al. (1988). A superscript "S" indicates availability from the Corn Genetic Stock Center, Department of Agronomy, University of Illinois (Urbana).

EXAMPLE 6

Imparting Male Sterility to Selected Lines

In addition, various approaches to imparting male sterility in corn can be used to produce male-sterile, low saturate material within the present invention, which material can be employed in turn to produce hybrids which also display a low saturate phenotype according to the present invention. An inbred line possessing such a low saturate phenotype can thus be advantageously employed in a backcrossing program as a recurrent parent to cytoplasmic-genetic, male-sterile donors containing both nuclear and cytoplasmic factors imparting male sterility (A lines), to donors containing nuclear but not cytoplasmic factors imparting male sterility (B lines), and to donors containing nuclear and cytoplasmic factors that restore fertility to male-sterile material (R lines), as described, for example, by Coe et al. (1988), at pages 195–98 and pages 206–09, and Poehlman, "Breeding Field Crops" (2d ed.), AVI Publishing Co. (1979), at pages 292–95. Sources for cytoplasmic male-sterility (cms) and fertility restoration (Rf) factors include Holden's Foundation Seeds, Inc., P.O. Box 839, Williamsburg, Iowa 52361 (cms-S and cms-C); Illinois Foundation Seeds, Inc., P.O. Box 722, Champaign, Ill. 61820 (cms-S and cms-C); and Agronomy Department, University of Illinois, Urbana, Ill. (cms-T, cms-S, cms-C and various Rf determinations).

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An asseblage of corn seeds, obtained from a plant or plants belonging to a corn line selected from the group consisting of LS0417 (ATCC Accession No. PTA-1397), LS1498 (ATCC Accession No. PTA-1396), and LS288 (ATCC Accession No. PTA-3642), said assemblage having a mean saturate content of less than about 7.0%, a mean oleic acid content of at least 64.9%, and a mean linoleic acid content of 27.4% or less, by weight relative to the total fatty acid content of said seed.

2. The assemblage of corn seeds according to claim 1, wherein said mean saturate content is less than about 6.7% by weight.

3. The assemblage of corn seeds according to claim 1, wherein said mean saturate content is less than about 6.0% by weight.

4. The assemblage of corn seeds according to claim 1, wherein said seeds are obtained from a plant or plants belonging to the LS0417 (ATCC Accession No. PTA-1397) corn line.

5. The assemblage of corn seeds according to claim 1, wherein said seeds are obtain from a plant or plants belonging to the LS1498 (ATCC Accession No. PTA-1396) corn line.

6. A corn plant, belonging to a corn line selected from the group consisting of LAS0417 (ATCC Accession No. PTA-1397), LS1498 (ATCC Accession No. PTA-1396), and LS288 (ATCC Accession No. PTA-3642), said plant producing seeds having a mean saturate content of less than about 7.0%, a mean oleic acid content of at least 64.9%, and a mean linoleic acid content of 27.4% or less, by weight relative to the total fatty acid content of said seeds.

7. The corn plant according to claim 6, wherein said corn plant belongs to the LS0417 (ATCC Accession No. PTA-1397) corn line.

8. The corn plant according to claim 6, wherein said corn plant belongs to the LS1498 (ATCC Accession No. PTA-1396) corn line.

9. A method for producing low saturate corn material comprising the steps of:

(a) obtaining a plurality of corn seeds, from a plant or plants belonging to a corn line selected from the group consisting of LS0417 (ATCC Accession No. PTA-1397), LS1498 (ATCC Accession No. PTA-1396), and LS288 (ATCC Accession No. PTA-3642), said corn seeds having a mean saturate content of less than about 7.0%, a mean oleic acid content of at least 64.9%, and a mean linoleic acid content of 27.4% or less;

(b) growing out said plurality of corn seeds to obtain a population of corn plants;

(c) intermating plants from said population to produce first seeds;

(d) subjecting said first seeds to selection based on saturate content, such that a predetermined saturate percentage of said first seeds is retained to obtain a group of selected seeds;

(e) growing said selected seeds into plants;

(f) intermating said plants to produce second seeds; and (g) with said second seeds obtained, repeating steps (b), (c), (d), (e), and (f) at least once, whereby plants producing seeds that have a mean saturate content of less than about 7.0% by weight are obtained.

10. The assemblage of corn seeds according to claim 1, wherein said seeds are obtained from a plant or plants belonging to the LS288 (ATCC Accession No. PTA-3642) corn line.

11. The corn plant according to claim 6, wherein said plant belongs to the LS288 (ATCC Accession No. PTA-3642) corn line.

12. The method according to claim 9, wherein said corn seeds are obtained from a plant or plants from the LS0417 (ATCC Accession No. PTA-1397) corn line.

13. The method according to claim 9, wherein said corn seeds are obtained from a plant or plants from the LS1498 (ATCC Accession No. PTA-1396) corn line.

14. The method according to claim 9, wherein said corn seeds are obtained from a plant or plants from the LS288 (ATCC Accession No. PTA-3642) corn line.

15. A method for producing a first generation hybrid corn seed comprising the steps of:

crossing a plant according to claim 6 with a different inbred parent corn plant and harvesting the resultant first generation hybrid corn seed.

16. The method of claim 15, wherein the corn plant of claim 6 is the female or male parent.

17. Seed of corn inbred line designated LS0417, representative seed of the line having been deposited under ATCC Accession No. PTA-1397, and wherein the seed have a mean saturate content of less than about 7.0%, a mean oleic content of at least 64.9% and a mean linoleic acid content of 27.4% or less, by weight relative to the total fatty acid content of the seed.

18. Seed of corn inbred line designated LS1498, representative seed of the line having been deposited under ATCC Accession No. PTA-1396, and wherein the seed have a mean saturate content of less than about 7.0%, a mean oleic content of at least 64.9% and a mean linoleic acid content of 27.4% or less, by weight relative to the total fatty acid content of the seed.

19. Seed of corn inbred line designated LS288, representative seed of the line having been deposited under ATCC Accession No. PTA-3642, and wherein the seed have a mean saturate content of less than about 7.0%, a mean oleic content of at least 64.9% and a mean linoleic acid content of 27.4% or less, by weight relative to the total fatty acid content of the seed.

* * * * *